(12) United States Patent
Libbus et al.

(10) Patent No.: US 8,301,239 B2
(45) Date of Patent: Oct. 30, 2012

(54) SYSTEMS, DEVICES AND METHODS FOR ACUTE AUTONOMIC STIMULATION

(75) Inventors: Imad Libbus, St. Paul, MN (US); Stefan Nikles, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1047 days.

(21) Appl. No.: 11/624,300

(22) Filed: Jan. 18, 2007

(65) Prior Publication Data
US 2008/0177190 A1 Jul. 24, 2008

(51) Int. Cl.
*A61N 1/36* (2006.01)
(52) U.S. Cl. .................................. 607/2; 607/9; 607/116
(58) Field of Classification Search .................. 607/2, 4, 607/9, 116, 118, 124, 5, 115
See application file for complete search history.

(56) References Cited

U.S. PATENT DOCUMENTS

| | | | |
|---|---|---|---|
| 5,571,150 A | | 11/1996 | Wernicke et al. |
| 6,532,388 B1 * | | 3/2003 | Hill et al. ........................... 607/2 |
| 6,622,041 B2 | | 9/2003 | Terry, Jr. et al. |
| 6,692,490 B1 | | 2/2004 | Edwards |
| 6,735,471 B2 * | | 5/2004 | Hill et al. ........................... 607/2 |
| 7,769,446 B2 | | 8/2010 | Moffitt et al. |
| 7,783,349 B2 | | 8/2010 | Libbus et al. |
| 2002/0032468 A1 * | | 3/2002 | Hill et al. ........................... 607/2 |
| 2004/0044377 A1 | | 3/2004 | Larsson |
| 2004/0172075 A1 * | | 9/2004 | Shafer et al. ........................ 607/9 |
| 2006/0122675 A1 | | 6/2006 | Libbus et al. |
| 2007/0060954 A1 * | | 3/2007 | Cameron et al. .................... 607/2 |
| 2007/0150011 A1 | | 6/2007 | Meyer et al. |

FOREIGN PATENT DOCUMENTS

| | | |
|---|---|---|
| GB | 2294642 | 5/1996 |
| WO | WO-01/00273 A1 | 1/2001 |
| WO | WO 01/00273 A1 * | 1/2001 |
| WO | WO 0100273 A1 * | 1/2001 |
| WO | WO-2006/060458 A1 | 6/2006 |

OTHER PUBLICATIONS

"Heart Failure Post-Myocardial Infarction: A Review of the Issues," Dargie, H.; Heart; 2005; 91, (Suppl II: ii3-ii6. doi: 10.1136/hrt.2005. 062018.*
"International Application No. PCT/US2008/000511, International Search Report mailed Jun. 27, 2008", 4 pgs.
"International Application No. PCT/US2008/000511, Written Opinion mailed Jun. 27, 2008.", 6 pgs.
Kamath, M. V., et al., "Neurocardiac and Cerebral Responses Evoked by Esophageal Vago-Afferent Stimulation in Humans: Effect of Varying Intensities", *Cardiovascular Research*, 40(3), (1998), 591-599.

* cited by examiner

*Primary Examiner* — Carl H Layno
*Assistant Examiner* — Pamela M Bays
(74) *Attorney, Agent, or Firm* — Schwegman Lundberg & Woessner, P.A.

(57) ABSTRACT

Various system embodiments comprise a medical device, comprising a flexible tether, a neural stimulation circuit, and a controller. The flexible tether is adapted to be fed into a patient's throat. The flexible tether includes a plurality of electrodes. The neural stimulation circuit is adapted to deliver neural stimulation. The controller is adapted to control the neural stimulation circuit to provide a neural stimulation therapy using at least one electrode from the plurality of electrodes, and to implement a neural stimulation test routine. The neural stimulation test routine is adapted to assess neural stimulation efficacy for electrode subsets of the plurality of electrodes to identify a desired electrode subset for use in delivering the neural stimulation therapy to elicit a desired response.

22 Claims, 9 Drawing Sheets

SYSTEMS, DEVICES AND METHODS FOR ACUTE AUTONOMIC STIMULATION

FIELD

This application relates generally to medical devices and, more particularly, to systems, devices and methods for providing acute autonomic stimulation.

BACKGROUND

A reduced autonomic balance during heart failure has been shown to be associated with left ventricular dysfunction and increased mortality. This reduced autonomic balance increases sympathetic and decreases parasympathetic cardiac tone. Direct stimulation of the vagal parasympathetic fibers has been shown to reduce heart rate via activation of the parasympathetic nervous system and indirect inhibition of the sympathetic nervous system. Some data indicate that increasing parasympathetic tone and reducing sympathetic tone may protect the myocardium from further remodeling and predisposition to fatal arrhythmias following myocardial infarction; and some data indicates that chronic stimulation of the vagus nerve may protect the myocardium following cardiac ischemic insult. Vagus nerve stimulation increases parasympathetic tone and decreases sympathetic tone. However, implantation of electrodes is an invasive procedure, and it can be difficult to immediately implant electrodes after a myocardial infarction.

SUMMARY

Various system embodiments comprise a medical device, comprising a flexible tether, a neural stimulation circuit, and a controller. The flexible tether is adapted to be fed into a patient's throat. The flexible tether includes a plurality of electrodes. The neural stimulation circuit is adapted to deliver neural stimulation. The controller is adapted to control the neural stimulation circuit to provide a neural stimulation therapy using at least one electrode from the plurality of electrodes, and to implement a neural stimulation test routine. The neural stimulation test routine is adapted to assess neural stimulation efficacy for electrode subsets of the plurality of electrodes to identify a desired electrode subset for use in delivering the neural stimulation therapy to elicit a desired response.

Various system embodiments comprises means for automatically selecting at least one electrode from a plurality of electrodes located in a pharynx, a larynx, a trachea, or an esophagus of a patient. The means for selecting at least one electrode includes means for determining that the selected at least one electrode is effective for use in delivering neural stimulation to elicit a desired response. Various system embodiments further comprise means for automatically delivering a neural stimulation therapy using the selected at least one electrode.

According to various method embodiments, an emergency patient is identified as a candidate for post myocardial infarction (post-MI) neural stimulation therapy. A flexible tether of a portable device is inserted into the patient's throat. The flexible tether includes a plurality of electrodes. Autonomic neural stimulation is delivered to a desired neural target to elicit a desired neural response for the post-MI neural stimulation therapy.

A portable medical device embodiment comprises a flexible tether, a neural stimulation circuit, a battery terminal adapted to receive at least one battery, and a controller. The flexible tether is adapted to be fed into a patient's throat, and includes at least one neural stimulation element for use in delivering neural stimulation to a neural target. The neural stimulation circuit is adapted to deliver neural stimulation using the at least one neural stimulation element. The battery terminal is connected to the neural stimulation circuit and the controller to enable the at least one battery to power the neural stimulation circuit and the controller. The controller is adapted to control the neural stimulation circuit to provide an autonomic neural stimulation therapy using the at least one neural stimulation element. According to various embodiments, the neural stimulation element may be an electrode, a transducer adapted to deliver ultrasound energy, a transducer adapted to deliver light energy, a transducer adapted to deliver magnetic energy, or a transducer adapted to deliver thermal energy.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
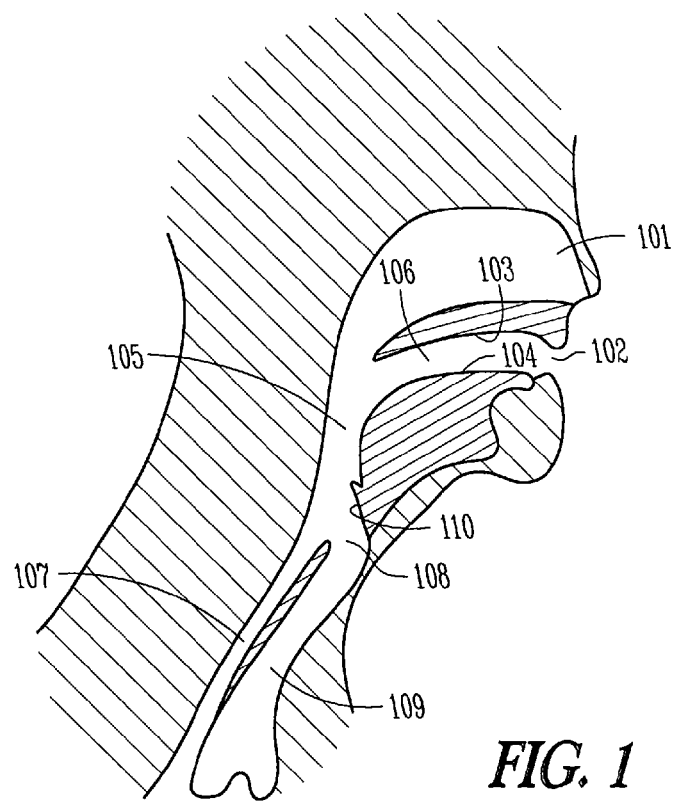
FIG. 1 illustrates the physiology of the upper respiratory/digestive systems.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter provides a portable, external device with a flexible tether adapted to pass electrode(s) through a patient's nose or mouth into, and in some embodiments through, the patient's throat. Various embodiments pass the stimulation electrode(s) through the patient's throat into the patient's trachea, using orotracheal intubation (passing the endotracheal tube through the mouth, through the larynx, and into the trachea) or using nasotracheal intubation (passing the tube through the nose, through the larynx, and into the trachea). Various embodiments pass the stimulation electrode(s) through the patient's throat into the patient's larynx. Various embodiments pass the stimulation electrode(s) through the patient's throat into the patient's esophagus. The electrode(s) are positioned to provide stimulation of the vagus nerve. Vagus nerve stimulation increases parasympathetic tone and decreases sympathetic tone.

In various embodiments, the flexible tether includes a flexible intubation tube to be placed in the patient's throat. The flexible intubation tube can be similar to tubes used in a transesophageal echocardiogram (TEE) system. The tube is designed to be inserted into the patient's throat, either passively (if the patient is conscious) or actively. For example, if the patient is conscious, the patient can swallow the tube to advance the tube into the throat, and to further advance the tube into the esophagus. If the patient is not conscious, the tube can be inserted through the nose or mouth into the throat. The end of the tube can be positioned in the pharynx, the larynx, the trachea or the esophagus. Sedatives can be administered to reduce discomfort and increase relaxation. A mouthpiece can be used to guide the tube into the throat. The tube itself can be lubricated to assist with the insertion procedure.

In various embodiments, the device is adapted to provide airway management. The tube includes an open lumen which is used in conjunction with an external air bladder for mechanical ventilation. For embodiments that provide airway management, the tube is inserted along the airway pathway (e.g. the end of the tube is positioned along the pathway that includes the pharynx, larynx, and trachea).

Various embodiments provide a plurality of stimulation electrodes on the external surface of the tube. These electrodes can be used to provide emergency parasympathetic stimulation by transesophageal activation of the vagus nerve (or branches thereof). In various embodiments, the tube contains one or more electrodes which is used to provide unipolar stimulation in conjunction with an external electrode, placed on the patient's skin. Various embodiments also use the counter electrode for other purposes (e.g. skin electrode for electrocardiogram recording, or for external pacing or defibrillation). Stimulation can occur from a intraesophageal electrode(s) with counter electrode(s) placed anywhere else on or in the body.

The portable external device can be used by a first responder, who may provide on-the-scene emergency parasympathetic stimulation. For example, this device may be used to provide parasympathetic therapy in the minutes or hours following an acute myocardial infarction (MI). Immediate therapy is known to be of critical importance in preventing cardiac damage following an acute MI.

Physiology of the Upper Respiratory/Digestive System and the Vagus Nerve

FIG. 1 illustrates the physiology of the upper respiratory/digestive systems. The figure illustrates a nasal cavity 101, and a mouth cavity 102 separating a soft palate 103 and tongue 104. The figure also illustrates a throat, generally identified as including a pharynx 105 and fauces 106. The term fauces refers to the space between the cavity of the mouth and the pharynx, bounded by the soft palate and the base of the tongue. The pharynx is part of the digestive system and respiratory system, and is situated posterior to the mouth and nasal cavity, and cranial to the esophagus 107, larynx 108 and trachea 109. The human pharynx can be divided into the nasopharynx (the region lying behind the nasal cavity), the oropharynx (the region lying behind the mouth cavity), and the hypopharynx, also knows as the laryngopharynx. The hypopharynx lies directly posterior to the upright epiglottis 110 and extends to the larynx, where the respiratory and digestive pathways diverge. The digestive pathway proceeds to the esophagus, and the respiratory pathway proceeds to the larynx and the trachea. The esophagus 107 conducts food and fluids to the stomach. Air enters the larynx anteriorly. The epiglottis 110 is a thin, lid-like flap of cartilage tissue attached to the root of the tongue that is normally pointed upward, but temporarily folds down over the entrance to the vocal cords to stop the air passage when swallowing solids or liquids to prevent food and water from passing into the trachea. The larynx 108 is an organ of voice production, as it houses the vocal cords, and is situated in the part of the respiratory tract just below where the tract of the pharynx splits into the trachea and the esophagus. The trachea 109, or windpipe, is the air tube extending from the larynx into the thorax.

Figure 2:
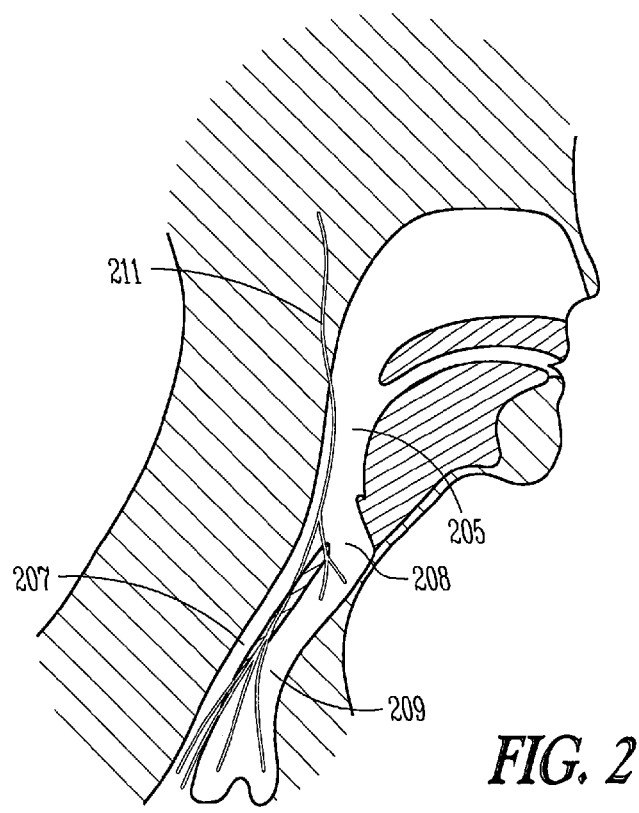
FIG. 2 illustrates the vagus nerve superimposed on the upper respiratory/digestive systems illustrated in FIG. 1.

FIG. 2 illustrates a vagus nerve 211 superimposed on the upper respiratory/digestive systems illustrated in FIG. 1. The vagus nerve 211 has a more extensive course and distribution than any of the other cranial nerves, since it passes through the neck and thorax to the abdomen. The vagus nerve supplies nerve fibers to the pharynx 205 (throat), larynx 208 (voice box), trachea 209 (windpipe), lungs, heart, esophagus 207, and the intestinal tract as far as the transverse portion of the colon. The vagus nerve also brings sensory information back to the brain from the ear, tongue, pharynx, and larynx.

As identified by Henry Gray's Anatomy of the Human Body, the distribution of the vagus nerve is complex. The vagus nerve passes vertically down the neck within the carotid sheath, lying between the internal jugular vein and internal carotid artery as far as the upper border of the thyroid cartilage, and then between the same vein and the common carotid artery to the root of the neck. The further course of the nerve differs on the two sides of the body. On the right side, the nerve passes across the subclavian artery between it and the right innominate vein, and descends by the side of the trachea to the back of the root of the lung, where it spreads out in the posterior pulmonary plexus. From the lower part of this plexus two cords descend on the esophagus, and divide to form, with branches from the opposite nerve, the esophageal plexus. Below, these branches are collected into a single cord, which runs along the back of the esophagus enters the abdomen, and is distributed to the postero-inferior surface of the stomach, joining the left side of the celiac plexus, and sending filaments to the lienal plexus. On the left side, the vagus enters the thorax between the left carotid and subclavian arteries, behind the left innominate vein. It crosses the left side of the arch of the aorta, and descends behind the root of the left lung, forming there the posterior pulmonary plexus. From this it runs along the anterior surface of the esophagus, where it unites with the nerve of the right side in the esophageal plexus, and is continued to the stomach, distributing branches over its anterosuperior surface; some of these extend over the fundus, and others along the lesser curvature. Filaments from these branches enter the lesser omentum, and join the hepatic plexus.

The branches of distribution of the vagus nerve in the neck include the pharyngeal, superior laryngeal, recurrent and superior cardiac branches. The branches of distribution of the vagus nerve in the thorax include the inferior cardiac, anterior bronchial, posterior bronchial, and esophageal branches. The pharyngeal branch is the principal motor nerve of the pharynx. The superior laryngeal nerve descends by the side of the pharynx, behind the internal carotid artery, and divides into external and internal branches. The external branch of the superior laryngeal nerve descends on the larynx, branches to the pharyngeal plexus and communicates with the superior cardiac nerve. The internal branch of the superior laryngeal nerve is distributed to the mucous membrane of the larynx, where some branches are distributed to the epiglottis and other pass backward to supply the mucous membrane surrounding the entrance of the larynx. The right side of the recurrent branch ascends obliquely to the side of the trachea behind the common carotid artery, and the left side of the recurrent branch ascends to the side of the trachea. On either side, the recurrent nerve ascends in the groove between the trachea and esophagus, and enters the larynx. As the recurrent nerve ascend in the neck, it branches to the mucous membrane and muscular coat of the esophagus, the mucous membrane and muscular fibers of the trachea, and some pharyngeal filaments branch to the constrictor pharyngis inferior. The esophageal branches form the esophageal plexus.

This brief discussion illustrates that there are a number of vagus nerve sites along the digestive and respiratory pathways. The present subject matter provides stimulation electrode(s) within the digestive pathway, the respiratory pathway or both the digestive and respiratory pathways for use in delivering neural stimulation that targets at least some of these vagus nerve sites.

Embodiments for Positioning Flexible Tether

Figure 3:
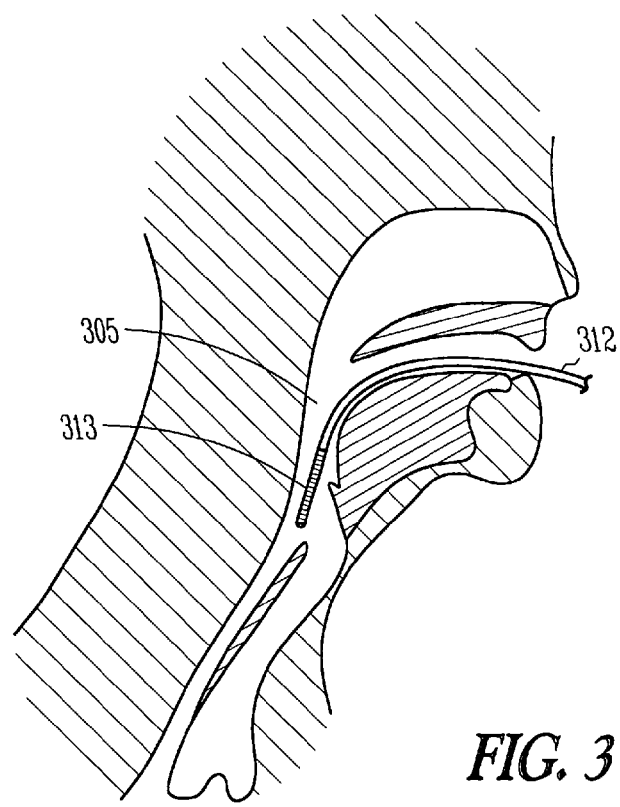
FIG. 3 illustrates an embodiment where a flexible tether is fed through a mouth into a patient's throat to position electrode(s) in the pharynx.

FIG. 3 illustrates an embodiment where a flexible tether 312 is fed through a mouth into a patient's throat to position electrode(s) in the pharynx 305. The illustrated flexible tether includes one electrode region 313 at or near the distal portion of the lead. The electrode region includes a number of potential electrodes capable of being selected for use to deliver the neural stimulation.

Figure 4:
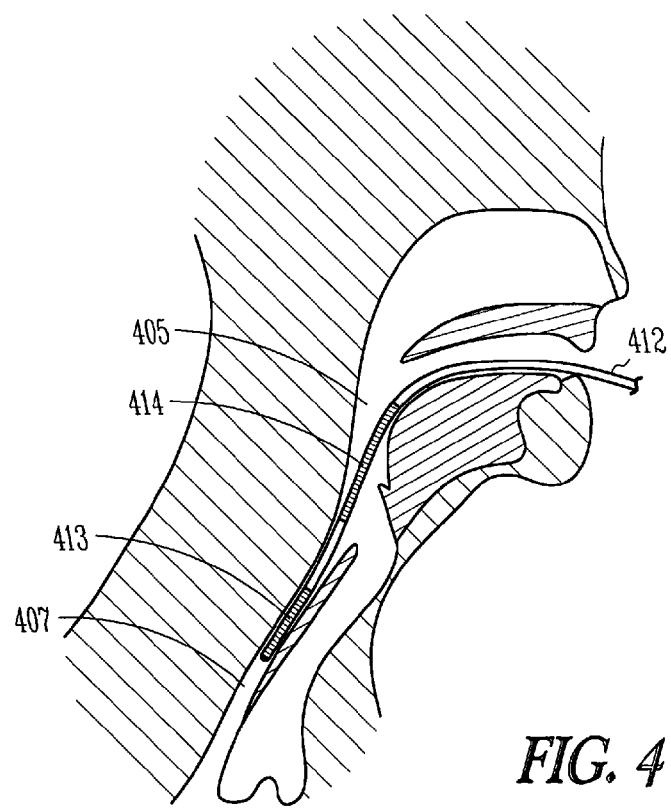
FIG. 4 illustrates an embodiment where a flexible tether is fed through a mouth into a patient's throat to position electrode(s) in the esophagus, and to also position electrodes in the pharynx.

FIG. 4 illustrates an embodiment where a flexible tether 412 is fed through a mouth into a patient's throat to position electrode(s) in the esophagus 407, and to also position electrodes in the pharynx 405. The illustrated flexible tether includes a first electrode region 413 at or near the distal portion of the lead, which is illustrated as being positioned in the esophagus. Also, as illustrated, various embodiments of the flexible tether provide a second electrode region 414, illustrated as being positioned in the pharynx. Each of the electrode regions includes a number of potential electrodes capable of being selected for use to deliver the neural stimulation. Some embodiments provide a larger electrode region that encompasses the illustrated first and second electrode regions. Some tether embodiments provide additional electrode regions.

Figure 5:
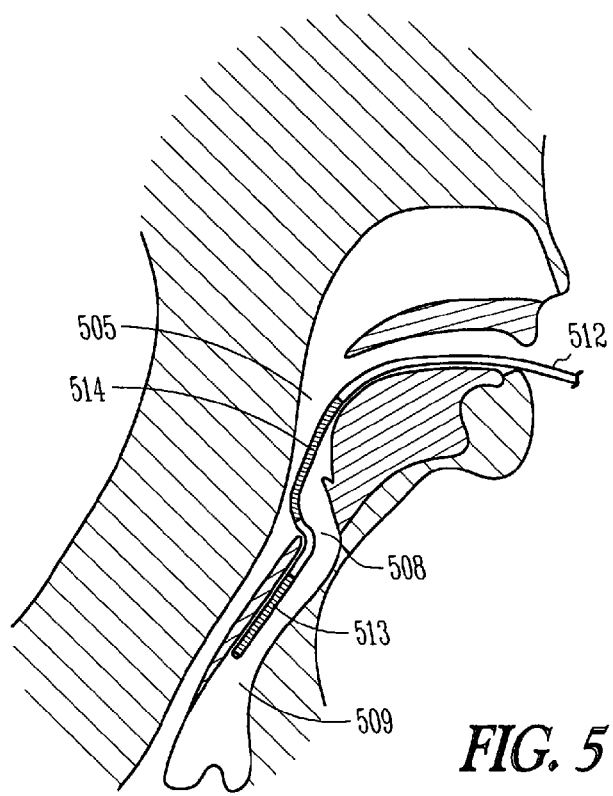
FIG. 5 illustrates an embodiment where a flexible tether is fed through a mouth into a patient's throat to position electrode(s) in the trachea, and to also position electrodes in the pharynx and/or larynx.

FIG. 5 illustrates an embodiment where a flexible tether 512 is fed through a mouth into a patient's throat to position electrode(s) in the trachea 509, and to also position electrodes in the pharynx 505 and/or larynx 508. The illustrated flexible tether includes a first electrode region 513 at or near the distal portion of the lead, which is illustrated as being positioned in the trachea. Also, as illustrated, various embodiments of the flexible tether provide a second electrode region 514, illustrated as being positioned in the pharynx and/or larynx. Each of the electrode regions includes a number of potential electrodes capable if being selected for use to deliver the neural stimulation. Some embodiments provide a larger electrode region that encompasses the illustrated first and second electrode regions. Some tether embodiments provide additional electrode regions.

Figure 6:
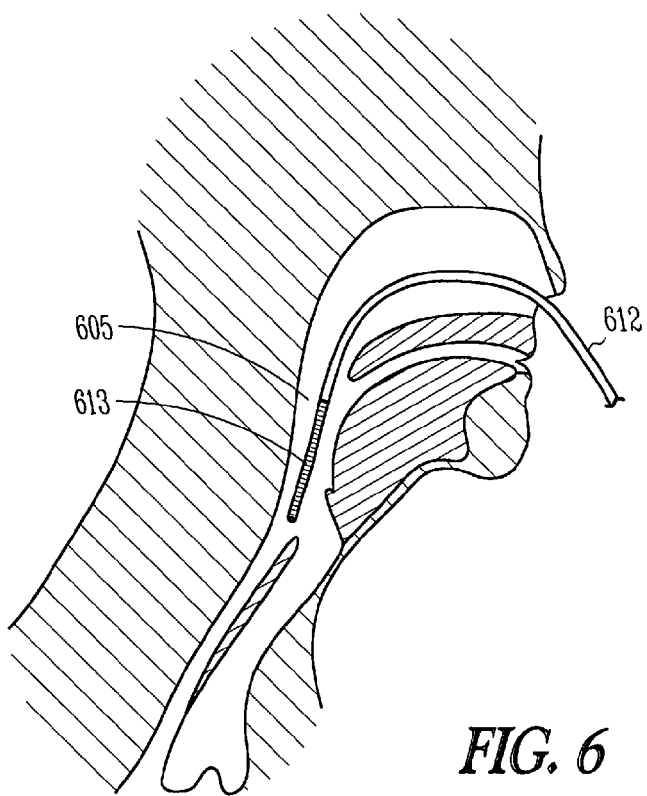
FIG. 6 illustrates an embodiment where a flexible tether is fed through a nose into a patient's throat to position electrode(s) in the pharynx.

FIG. 6 illustrates an embodiment where a flexible tether 612 is fed through a nose into a patient's throat to position electrode(s) in the pharynx 605. The illustrated flexible tether includes one electrode region 613 at or near the distal portion of the lead. The electrode region includes a number of potential electrodes capable of being selected for use to deliver the neural stimulation. The tether fed through the nose cavity can further be fed into the esophagus or the trachea, similar to the tethers illustrated in FIGS. 4 and 5. More than one electrode region can also be implemented on the flexible tether.

Various embodiments deliver electrode regions in various combinations of the pharynx, the larynx, the trachea and the esophagus using one or more tethers. The electrode regions positioned in these areas can be used to create stimulation vectors between two or more of the pharynx, the larynx, the trachea and the esophagus.

System Embodiments

Figure 7:
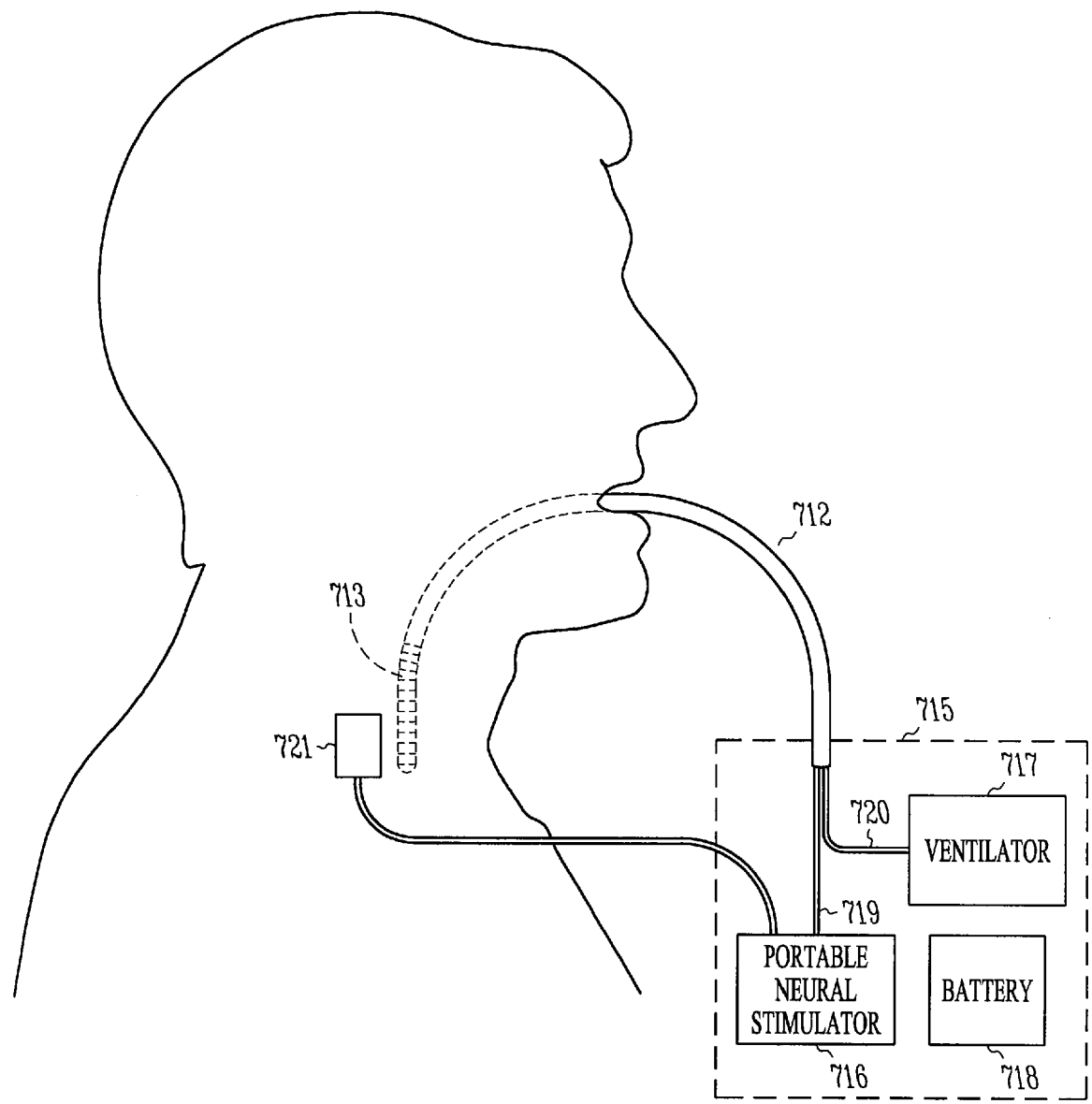
FIG. 7 illustrates an embodiment of a portable neural stimulator with at least one electrode in the respiratory or digestive pathway and a counter electrode on a patient's skin.

FIG. 7 illustrates an embodiment of a portable neural stimulator with at least one electrode in the respiratory or digestive pathway and a counter electrode on a patient's skin. The illustrated position of the counter electrode is provided as an example. Those of ordinary skill in the art will understand, upon reading and comprehending this disclosure, that the counter electrode can be placed elsewhere on the patient's skin, such as locations on the neck, chest, back and the like. The figure illustrates a portable device 715 that includes the portable neural stimulator 716 and a mechanical ventilator 717, both powered by a battery source 718. Some embodiments provide the mechanical ventilator and the neural stimulator as separate devices with separate power sources. Various embodiments do not include a mechanical ventilator.

A flexible tether 712 is illustrated as being fed through the mouth to place an electrode region 713 in the pharynx of the patient. The flexible tether 712 includes electrical conductor(s) 719 connected to the electrode(s) in the electrode region, and further includes a tube 720 adapted to deliver gas to the patient. Various embodiments provide the conductor(s) 719 and tube 720 in a separate sheathing. Various embodiments route the conductor(s) 719 within the tube 720. Various embodiments route the conductor(s) 719 on the external wall of the tube 720. In various embodiments, the flexible tube 720 is formed with conductive traces that are used to provide the conductor(s) to the electrode region. The conductor(s) are electrically insulated to prevent unwanted shocks to the tongue, mouth, and the like. The illustrated neural stimulator 716 is also connected to a counter electrode 721 positioned on the patient's skin. Various embodiments use a patch with an adhesive for securing the patch and the counter electrode(s) to the patient's skin. Electrical vectors can be provided between or among electrodes on the flexible tether and counter electrode(s) on the patient's skin. More than one counter electrode per patch, and more than one patch can be used (for example, a patch on the neck, a patch on the back, a patch on the chest, or various combinations thereof). Given the position and number of stimulation electrodes, some device embodiments are capable of delivering unipolar stimulation, bipolar stimulation, multipolar stimulation, or various combination thereof to provide a number of stimulation vectors. Various counter electrode embodiments include surface electrodes placed on the surface of the skin, and various counter electrode embodiments include percutaneous electrodes. Various embodiments use the counter electrode(s) to sense heart rate or blood pressure.

Figure 8:
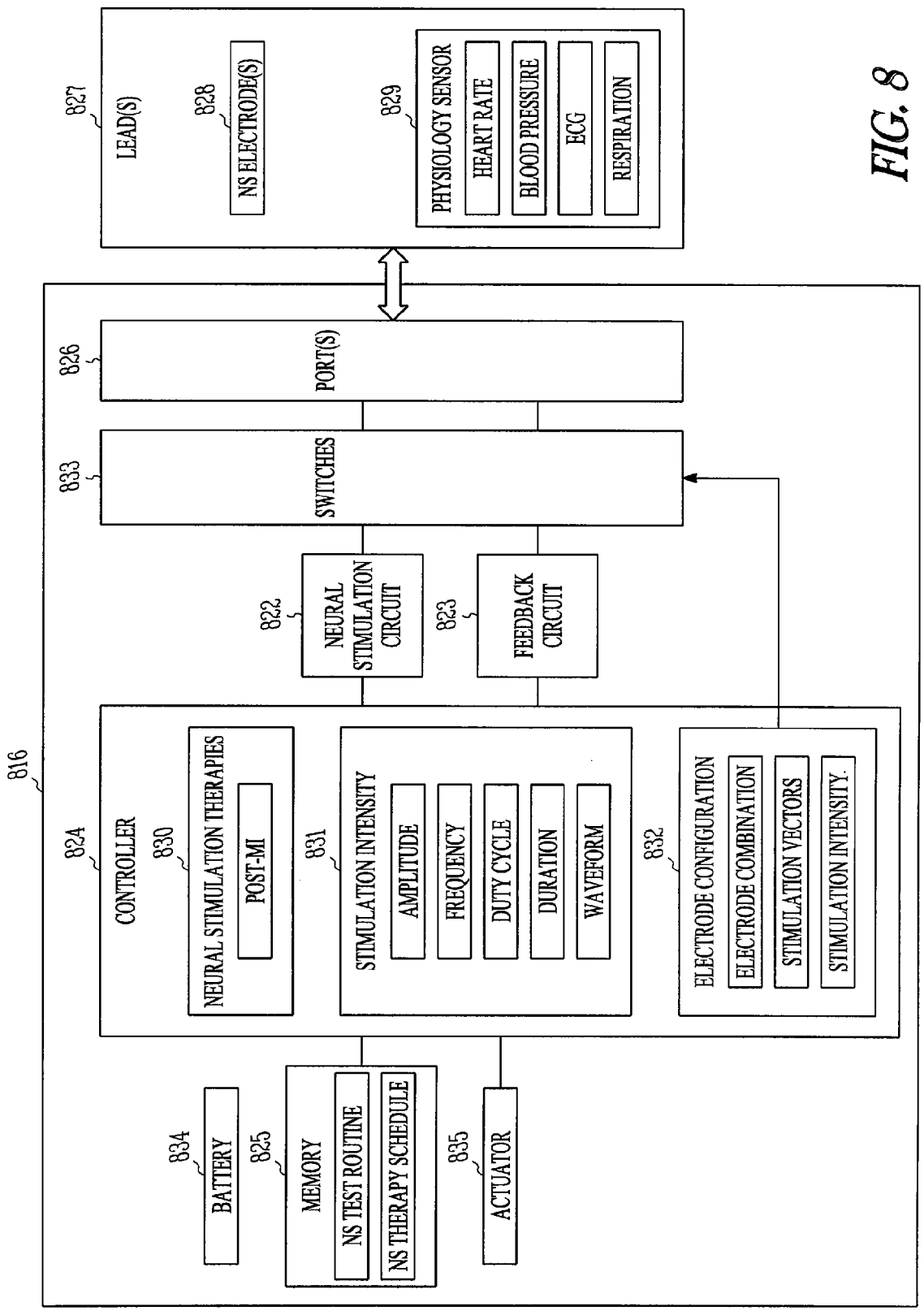
FIG. 8 illustrates various embodiments of a portable neural stimulator to stimulate the vagus nerve.

FIG. 8 illustrates various embodiments of a portable neural stimulator to stimulate the vagus nerve. The illustrated neural stimulator embodiment 816 includes a neural stimulation circuit 822, a feedback circuit 823, a controller 824, and memory 825. The illustrated embodiment further includes at least one port 826 to connect to at least one lead 827. The flexible tether illustrated in previous figures can function as a lead. A lead can also be used to connect the counter electrode to the neural stimulator. The neural stimulation circuit is connected to the port(s) to provide a neural stimulation signal to at least one neural stimulation electrode 828 on the lead(s) to elicit a vagus nerve response when an appropriate signal is provided to an appropriately-positioned neural stimulation electrode. The feedback circuit 823 is connected to the port(s) to receive a signal from the physiology sensor 829. The sensor senses a physiology function that depends, at least in part, on vagal stimulation. Examples of such functions includes heart rate, blood pressure, ECG waveforms, and respiration. Thus, various embodiments implement a heart rate sensor as the physiology sensor, and various embodiments implement a blood pressure sensor as the physiology sensor. Various embodiments provide a sensor capable of directly detecting the heart rate from the carotid artery, and various embodiments provide a sensor capable of directly detecting blood pressure from the carotid artery. One example of such a sensor is an acoustic sensor adapted to sense blood flow. The sensed blood flow is capable of being used to determine blood pressure and/or heart rate. However, other sensor technology can be used.

The memory 825 includes computer-readable instructions that are capable of being operated on by the controller to perform functions of the device. Thus, in various embodiments, the controller is adapted to operate on the instructions to provide programmed neural stimulation therapies 830 such as post-MI according to a neural stimulation therapy schedule stored in the memory. Various "closed loop" systems vary the intensity of the neural stimulation, as generally illustrated by the stimulation intensity module 831, based on the sensed physiology signal received by the feedback circuit according to a preprogrammed therapy to provide a desired affect. Thus, the closed loop system is capable of reducing and increasing the neural stimulation intensity as appropriate to maintaining some measured physiological parameters within an upper and lower boundary during the vagal stimulation therapy. Various "open loop" systems without feedback from the physiology signal also can be programmed to vary the stimulation intensity. Various embodiments modulate the stimulation intensity by modulating the amplitude of the neural stimulation signal, the frequency of the neural stimulation signal, the duty cycle of the neural stimulation signal, the duration of a stimulation signal, the waveform of the neural stimulation signal, the polarity of the neural stimulation signal, or any combination thereof.

Various embodiments automatically change the electrode configuration, as generally illustrated by the electrode configuration module 832 of the controller 824. The illustrated electrode configuration module 832 is adapted to control switches 833 to control which electrodes of the available electrodes are used to deliver the neural stimulation, and the stimulation vectors for the electrodes. Additionally, the illustrated electrode configuration module 832 is adapted to work with the stimulation intensity module 831 to control the stimulation intensity for the different electrode combinations and stimulation vectors. Thus, for example, the electrode configuration module 832 can find a reference neural stimulation level for a particular electrode combination and vector, and the stimulation intensity module 831 can further modulate the neural stimulation based on the reference neural stimulation level. A neural stimulation test routine stored in the memory 825 controls the process of testing for an efficacious electrode configuration from the available electrode configurations.

The illustrated device is a portable device, that is illustrated as being powered by a battery 834, which can be easily removed and replaced from a battery terminal of the device. The portable device also includes an actuator 835. In various embodiments, the actuator is used to initiate the neural stimulation test routine, and automatically deliver the neural stimulation therapy upon completion of the neural stimulation test routine. Thus, for example, an emergency responder can feed the flexible tube into a patient's throat, and then actuate the device to initiate the neural stimulation test routine, and automatically deliver the neural stimulation therapy upon completion of the neural stimulation test routine. The actuator can be a mechanical switch on the housing of the portable device. The mechanical switch can also power up the device, and initiate the test routine after power up. Various embodiments use a display and user interface(s), such as a touch screen, as an actuator to initiate the test routine. Various embodiments use an interface with one button or switch used to initiate the test routine for selecting the electrode configuration, and another button or switch to turn the stimulation therapy on or off. Various interface embodiments respond to voice commands. A simple, automated interface can step a user through the process, allowing the user to accurately deliver the therapy without significant, special training to operate the device. In various embodiments, the controller automatically implements the neural stimulation test routine. In various embodiments, the controller and user interface cooperate to implement a neural stimulation test routine to allow a user to select the at least one of the neural stimulation electrodes to use in delivering the autonomic neural stimulation therapy. For example, the user interface can display test results for various electrode configurations. The information identifying the electrode configurations can include the electrodes used in the stimulation, the stimulation amplitude, the stimulation frequency, the stimulation duty cycle, the stimulation duration, the stimulation waveform, and the stimulation polarity. The test results can include the detected physiologic response (e.g. heart rate) attributed to the neural stimulation for an electrode configuration. The user can review the test results, and select an electrode configuration using the test results.

Electrode Configurations

The neural stimulation test routine is adapted to assess neural stimulation efficacy for electrode subsets of a plurality of electrodes to identify a desired electrode subset for use in delivering the neural stimulation therapy to elicit a desired response. Each electrode subset of the plurality of electrodes includes at least one electrode. The electrode subsets can include various combinations of electrodes selected from the plurality of electrodes, including all of the electrodes in the plurality of electrodes.

A number of electrode configurations can be used. The illustrations included herein are provided as examples, and are not intended to be an exhaustive listing of possible configurations.

Figure 9:
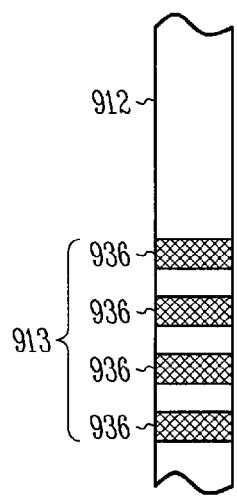
FIG. 9 illustrates an embodiment of a tether with annular stimulation electrodes, according to various embodiments.

FIG. 9 illustrates an embodiment of a tether 912 with annular stimulation electrodes 936 that form an electrode region 913, according to various embodiments. Any one or combination of the annular stimulation electrodes can be used to deliver the neural stimulation.

Figure 10A:
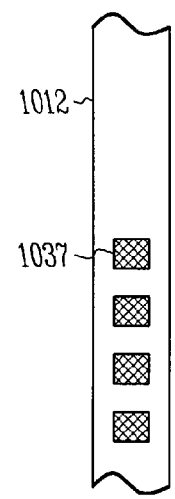
FIGS. 10A and 10B illustrate an embodiment of a tether with stimulation electrodes, where the illustrated electrodes do not circumscribe the tether.
Figure 10B:
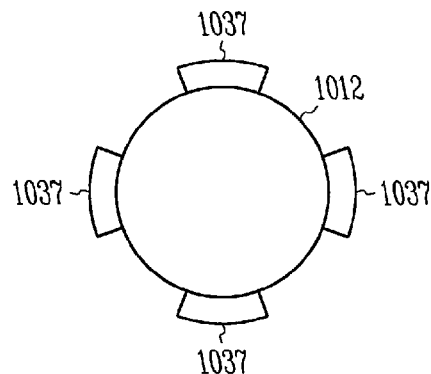

FIGS. 10A and 10B illustrate an embodiment of a tether 1012 with stimulation electrodes 1037, where the illustrated electrodes do not circumscribe the tether. Thus, a subset of the illustrated electrodes can be selected to provide directional stimulation. For example, the tether may twist or rotate as it is fed into a patient's throat, and it may be desired to stimulate a neural target on one side of the tether without stimulating other nerves or tissue on the other sides of the tether. A neural stimulation test routine can cycle through the available electrodes for use in delivering the neural stimulation to determine which subset of electrodes are facing toward the neural target.

Figure 11:
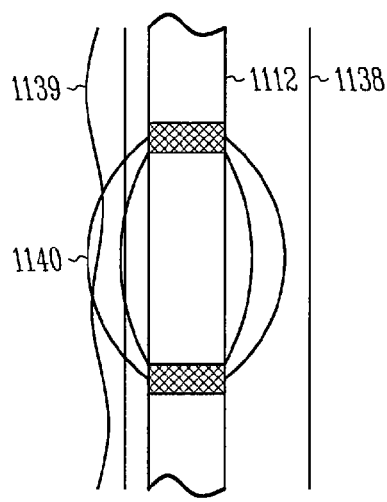
FIG. 11 illustrates a transluminal neural stimulation using electrodes within the lumen, according to various embodiments.

FIG. 11 illustrates a transluminal neural stimulation using electrodes within the lumen, according to various embodiments. The figure illustrates a lumen 1138 (e.g. trachea, esophagus, pharynx, larynx), a nerve 1139 external to the lumen, and a flexible tether 1112 within the lumen. The neural stimulation generates an electrical field 1140 between the electrodes that extends past the lumen wall to the nerve. As the vagus innervates the pharynx, larynx, trachea and esophagus, nerve endings may be stimulated in the lumen wall as well.

Figure 12:
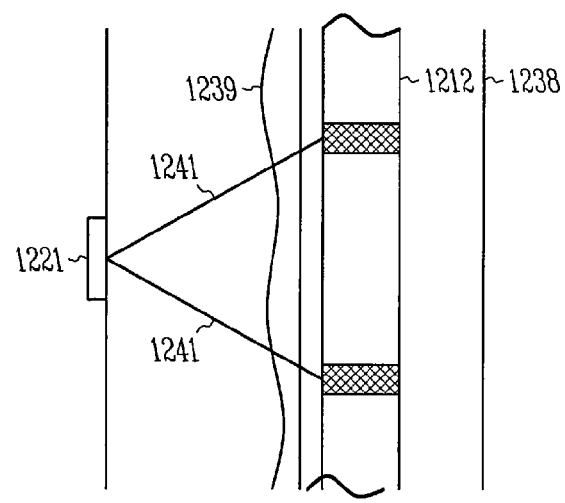
FIG. 12 illustrates neural stimulation using an external counter electrode, according to various embodiments.

FIG. 12 illustrates neural stimulation using an external counter electrode, according to various embodiments. The figure illustrates a lumen 1238 (e.g. trachea, esophagus, pharynx, larynx), a nerve 1239 external to the lumen, a flexible tether 1212 within the vessel, and a counter electrode 1221 on the patient's skin (e.g. neck). The neural stimulation generates an electrical vectors 1241 between the electrodes that extends past the vessel wall to the nerve.

FIGS. 13A through 13E are illustrations of electrode configurations used by the present system, according to various embodiments. In the embodiment illustrated in FIG. 13A, a first electrode configuration 1351 is used to deliver neural stimulation by generating an electrical signal from electrode A to electrode B. In this embodiment, if an efficacy of the first electrode configuration is lower than a threshold, the system switches to a second electrode configuration 1352 to deliver neural stimulation by generating an electrical signal from electrode C to electrode D. Electrodes A, B, C and D may be part of the same electrode region or may be different electrode regions, in various embodiments.

Figure 13A:
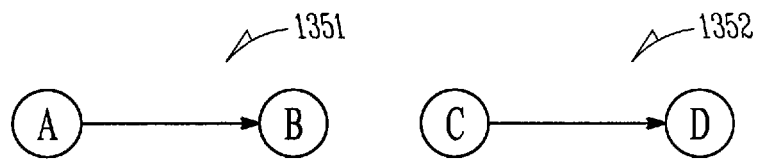
FIGS. 13A through 13E are illustrations of electrode configurations used by the present system, according to various embodiments.
Figure 13B:
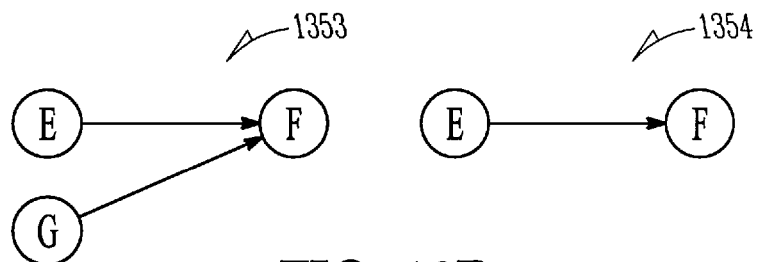

In the embodiment illustrated in FIG. 13B, a first electrode configuration 1353 is used to deliver neural stimulation by generating an electrical signal from electrode E to electrode F and from electrode G to electrode F. In this embodiment, if an efficacy of the first electrode configuration is lower than a threshold, the system switches to a second electrode configuration 1354 by removing an electrode (here electrode G) to deliver neural stimulation by generating an electrical signal from electrode E to electrode F. Electrodes E, F and G may be part of the same electrode region or may be different electrode regions, in various embodiments.

Figure 13C:
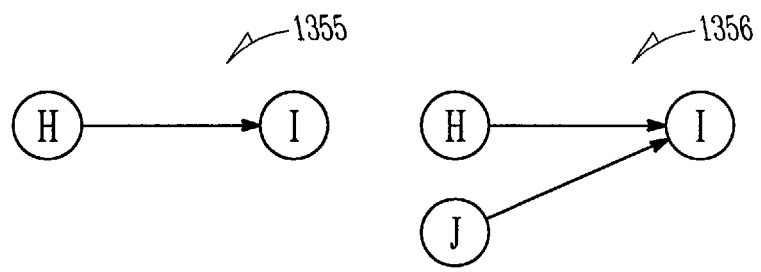

In the embodiment illustrated in FIG. 13C, a first electrode configuration 1355 is used to deliver neural stimulation by generating an electrical signal from electrode H to electrode I. In this embodiment, if an efficacy of the first electrode configuration is lower than a threshold, the system switches to a second electrode configuration 1356 by adding an electrode (here electrode J) to deliver neural stimulation by generating an electrical signal from electrode H to electrode I and from electrode J to electrode I. Electrodes H, I and J may be part of the same electrode region or may be different electrode regions, in various embodiments.

Figure 13D:
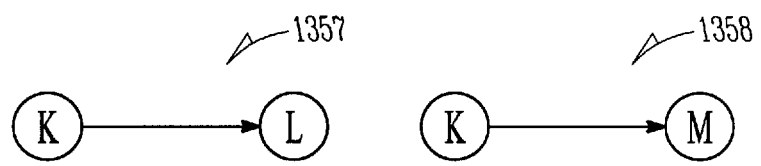

In the embodiment illustrated in FIG. 13D, a first electrode configuration 1357 is used to deliver neural stimulation by generating an electrical signal from electrode K to electrode L. In this embodiment, if an efficacy of the first electrode configuration is lower than a threshold, the system switches to a second electrode configuration 1358 by generating an electrical signal from electrode K to electrode M. Electrodes K, L and M may be part of the same electrode region or may be different electrode regions, in various embodiments.

Figure 13E:
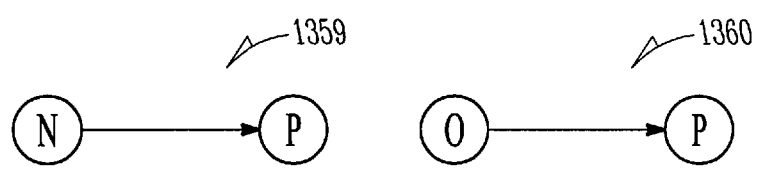

In the embodiment illustrated in FIG. 13E, a first electrode configuration 1359 is used to deliver neural stimulation by generating an electrical signal from electrode N to electrode P. In this embodiment, if an efficacy of the first electrode configuration is lower than a threshold, the system switches to a second electrode configuration 1360 by generating an electrical signal from electrode O to electrode P. Electrodes N, O and P may be part of the same electrode region or may be different electrode regions, in various embodiments. Other embodiments of electrode configurations that are adapted to stimulate a neural target are within the scope of this disclosure. In various embodiments, switching electrode configuration changes stimulation from bipolar to unipolar. In various embodiments, switching electrode configuration changes stimulation among a unipolar stimulation, a bipolar stimulation, or a multipolar stimulation. FIGS. 13A-13E refer to switching from one configuration to another configuration. Those of ordinary skill in the art will understand, upon reading and comprehending this disclosure, that the neural stimulation test routine is capable of switching among many electrode configurations, including the switched electrode configurations illustrated in FIGS. 13A-13E. Various embodiments use current steering to change the direction of current flow. For example, in situations where current flows from both a first and second electrode to a third electrode, the stimulation parameters can be adjusted, such as by changing the applied potential between electrodes, to change the stimulation intensity and location between the first and third electrodes and between the second and third electrodes.

Testing Electrode Configurations And Neural Stimulation

Figure 14:
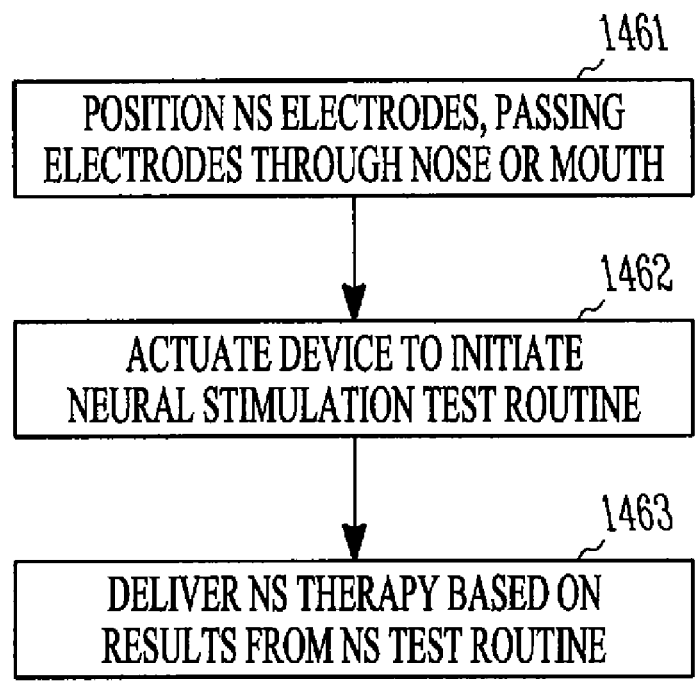
FIG. 14 illustrates a method for using the portable neural stimulator, according to various embodiments.

FIG. 14 illustrates a method for using the portable neural stimulator, according to various embodiments. An emergency responder, for example, can position the neural stimulation electrodes within the patient, as illustrated at 1461. The electrodes can be passed through the nose or mouth of the patient into the patients pharynx. The electrodes can be further passed into the esophagus, larynx or trachea of the patient. At 1462, the emergency responder actuates the device to initiate the neural stimulation test routine to determine an electrode configuration that can be used to deliver effective neural stimulation. At 1463, the neural stimulation is delivered based on the results of the neural test routine. In various embodiments, the neural stimulation is automatically delivered using an electrode configuration determined by the test routine to be able to be used to deliver effective neural stimulation. In various embodiments, the test routine provides results to the emergency responder, who can use the results to select an electrode configuration determined by the test routine to be able to be used to deliver effective neural stimulation.

Figure 15:
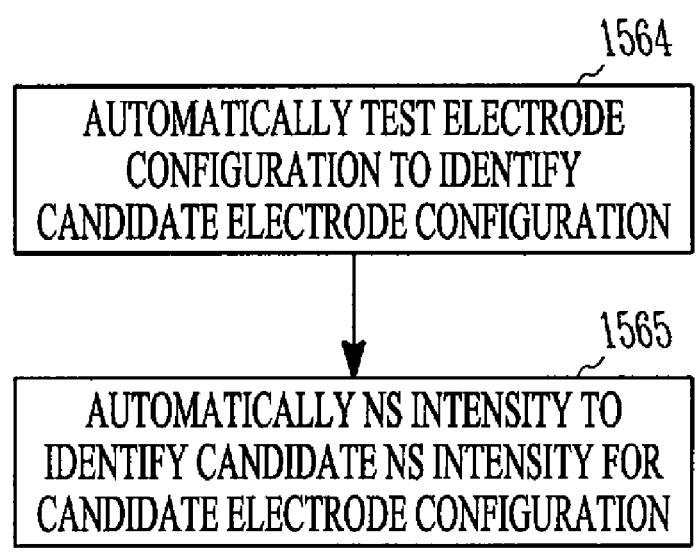
FIG. 15 illustrates a method for automatically performing a neural stimulation test routine, according to various embodiments.

FIG. 15 illustrates a method for automatically performing a neural stimulation test routine, according to various embodiments. In the illustrated embodiment, the electrode configuration is automatically tested, as illustrated at 1564, to identify an electrode configuration that is a candidate for use in delivering the neural stimulation therapy. For example, a candidate electrode configuration can be a configuration where neural stimulation provides a discernable effect, although not as efficacious as desired. Once a candidate electrode configuration is identified, the process proceeds to 1565, where the neural stimulation intensity is automatically tested to identify a candidate neural stimulation intensity for the candidate electrode configuration. Various embodiments continue the test, collecting data corresponding to different candidate electrode configurations and different candidate neural stimulation intensities to assess whether a candidate is more or less effective than other candidates. Various embodiments deliver the neural stimulation therapy using the first effective electrode configuration candidate and neural stimulation candidate.

Figure 16:
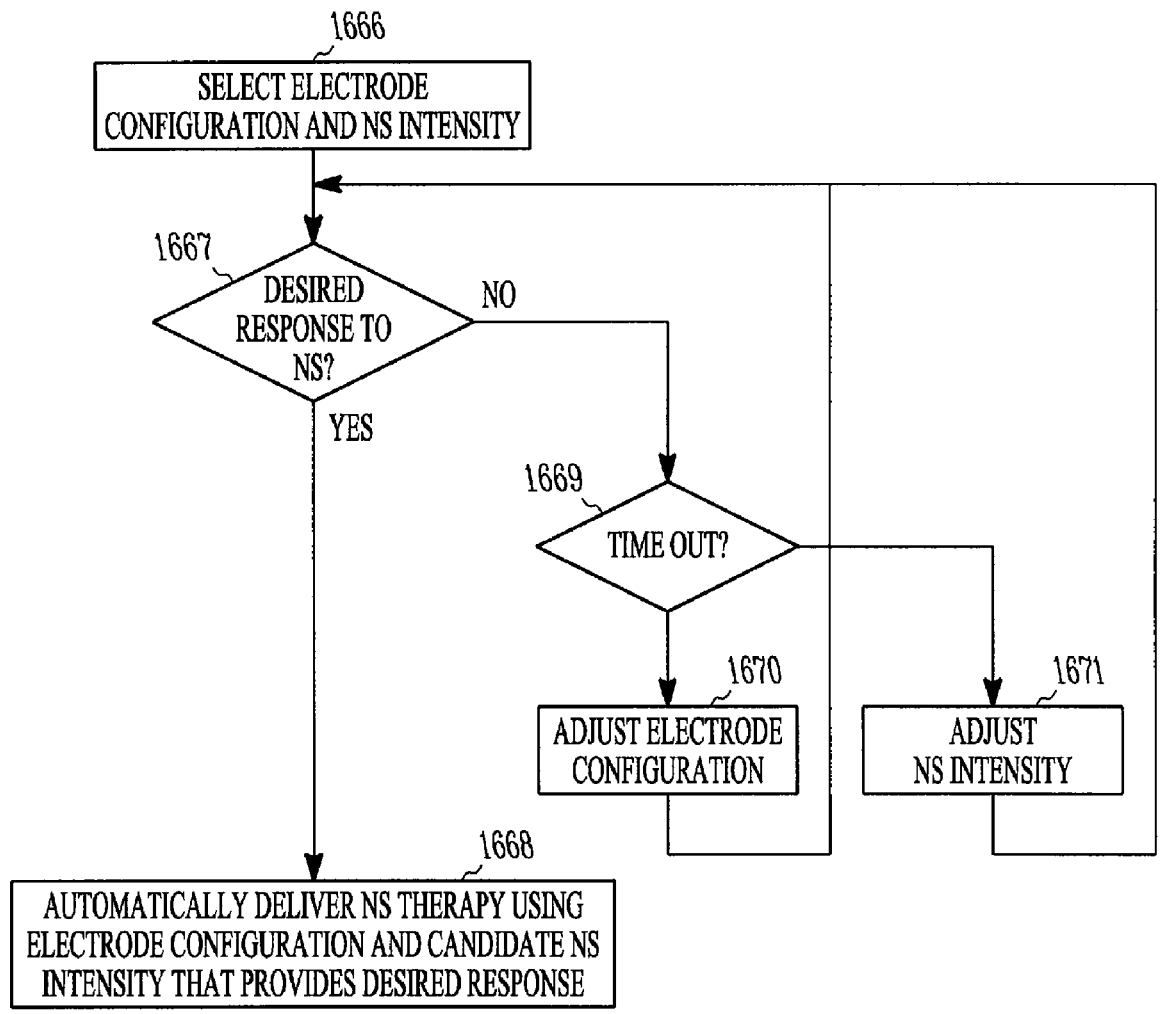
FIG. 16 illustrates a method for automatically performing the neural stimulation test routine, according to various embodiments.

FIG. 16 illustrates a method for automatically performing the neural stimulation test routine, according to various embodiments. At 1666, an electrode configuration and neural stimulation intensity is selected. At 1667, it is determined whether there is a desired response to neural stimulation using the selected electrode configuration and neural stimulation intensity. If there is a desired response, the process proceeds to 1668 to automatically deliver neural stimulation using the electrode configuration and a candidate neural stimulation intensity that provides the desired response. If a desired response is not detected and if a time out flag is not received at 1669, the process proceeds to 1670 to adjust the electrode configuration from the current electrode configuration to an another electrode configuration (e.g. different electrodes, electrode combinations, vectors). If the electrode configuration adjustments do not provide a desired response after a predetermined time or available electrode configurations have been exhausted, the process for selecting an electrode configuration times out at 1669, and the neural stimulation intensity is adjusted at 1671. After the neural stimulation intensity is adjusted, the process again determines whether there is a desired response to neural stimulation at 1667 and adjusts the electrode configuration until there is a desired response to the neural stimulation or until the process times out at 1669. If the process times out, the neural stimulation intensity can be adjusted again at 1671. According to various embodiments, the illustrated method is an automatic process that is initiated by an actuator on the portable neural stimulator.

According to various embodiments, the device, as illustrated and described above, is adapted to deliver neural stimulation as electrical stimulation to desired neural targets, such as through one or more stimulation electrodes positioned at predetermined location(s). Other elements for delivering neural stimulation can be used. For example, some embodiments use transducers to deliver neural stimulation using other types of energy, such as ultrasound, light, magnetic or thermal energy.

One of ordinary skill in the art will understand that, the modules and other circuitry shown and described herein can be implemented using software, hardware, and combinations of software and hardware. As such, the terms module and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by a processor cause the processor to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A medical device for delivering emergency stimulation to an emergency patient who has suffered an acute myocardial infarction, the device comprising:
    a flexible tether adapted to be fed into a patient's throat, the flexible tether including a plurality of electrodes;
    a neural stimulation circuit adapted to deliver neural stimulation; and
    a controller adapted to control the neural stimulation circuit to deliver emergency parasympathetic stimulation as provide a post myocardial infarction therapy to protect against cardiac damage following the acute myocardial infarction using at least one electrode from the plurality of electrodes, the controller being adapted to implement a neural stimulation test routine, the neural stimulation test routine being adapted to assess neural stimulation efficacy for electrode subsets of the plurality of electrodes to identify a desired electrode subset for use in delivering neural stimulation to elicit a desired vagal nerve response that increases parasympathetic tone and decreases sympathetic tone, wherein the post myocardial infarction therapy is configured to protect against cardiac damage following the acute myocardial infarction by eliciting the desired vagal nerve response.

2. The device of claim 1, wherein the electrode subsets include an electrode subset with a single electrode and the desired electrode subset is the electrode subset with the single electrode, the device further comprising at least one counter electrode that is not included with the flexible tether for use in providing at least one stimulation vector between the counter electrode and the single electrode.

3. The device of claim 1, wherein the neural stimulation test routine is adapted to assess neural stimulation efficacy for at least two stimulation vectors available for the desired electrode subset.

4. The device of claim 1, wherein the neural stimulation test routine is adapted to assess neural stimulation efficacy for at least two neural stimulation intensity levels for the desired electrode subset.

5. The device of claim 1, wherein the flexible tether includes at least one lumen adapted to deliver a gas for use by the patient in breathing.

6. The device of claim 1, wherein the plurality of electrodes includes a plurality of electrodes that at least partially circumscribe a circumference of the flexible tether.

7. The device of claim 1, wherein at least some of the plurality of electrodes are adapted for use in detecting heart rate.

8. The device of claim 1, wherein at least some of the plurality of electrodes are adapted for use in detecting an electrocardiogram (ECG) signal.

9. The device of claim 1, wherein the device is a portable device, the portable device including a battery terminal for connection to a battery to power the portable device.

10. The device of claim 1, wherein the neural stimulation test routine is adapted to select a first electrode subset capable of being used in delivering the post myocardial therapy to elicit the desired vagal nerve response.

11. The device of claim 1, wherein the neural stimulation test routine is adapted to determine at least two electrode subsets capable of being used in delivering the post myocardial infarction therapy to elicit the desired vagal nerve response and to assess an efficacy of the at least two electrode subsets in eliciting the desired vagal nerve response, the neural stimulation test routine further being adapted to select an electrode subset that the neural stimulation test routine assesses to be most efficacious.

12. The device of claim 1, wherein the flexible tether includes at least two distinct electrode regions, each electrode region including a plurality of electrodes.

13. The device of claim 1, wherein the flexible tether is further adapted to be fed through the patient's throat into a pharynx, into a larynx, into an esophagus, or into a trachea.

14. A system for delivering emergency stimulation to an emergency patient who has suffered an acute myocardial infarction, the system comprising:
    means for selecting at least one electrode from a plurality of electrodes located in a pharynx, a larynx, a trachea, or an esophagus of a patient, including means for determining that the selected at least one electrode is effective for use in delivering neural stimulation to elicit a desired vagal nerve response that increases parasympathetic tone and decreases sympathetic tone; and
    means for delivering a post myocardial infarction therapy to protect against cardiac damage following the acute myocardial infarction, wherein the means for delivering the post myocardial infarction therapy is configured to use the selected at least one electrode following the acute myocardial infarction to deliver the neural stimulation as emergency parasympathetic stimulation to elicit the desired vagal nerve response that increases parasympathetic tone and decreases sympathetic tone.

15. The system of claim 14, wherein the means for selecting at least one electrode includes:
    means for monitoring at least one physiological parameter that depends, at least in part, vagal nerve activity; and
    means for delivering the autonomic neural stimulation using different electrodes to identify that the at least one electrode is operationally positioned with respect to a desired neural target to elicit the desired vagal nerve response as determined using the at least one physiological parameter.

16. The system of claim 14, wherein the means for selecting at least one electrode includes means for automatically selecting at least two electrodes, and the means for delivering the post myocardial infarction therapy includes means for transluminally delivering neural stimulation to a desired neural target using the selected at least two electrodes.

17. The system of claim 14, wherein the means for delivering the post myocardial infarction therapy includes means for delivering neural stimulation to a desired neural target using the selected at least one electrode and a counter electrode.

18. The system of claim 14, wherein the means for delivering the post myocardial infarction therapy includes a flexible tether, the system further comprising means for delivering a gas through a lumen in the tether for use by a patient in breathing.

19. The system of claim 14, further comprising a memory, wherein the means for delivering the post myocardial infarction therapy is configured to apply the post myocardial infarction therapy according to a schedule stored in the memory.

20. The system of claim 14, wherein the means for delivering the post myocardial infarction therapy includes a closed loop system configured to adjust an intensity of the neural stimulation to maintain the desired vagal nerve response of a physiological parameter between an upper boundary and a lower boundary to protect against cardiac damage following an acute myocardial infarction.

21. The system of claim 14, wherein the means for selecting the at least one electrode and the means for delivering the post myocardial infarction therapy are configured to assess neural stimulation efficacy for at least two stimulation vectors for the plurality of electrodes and assess neural stimulation efficacy for at least two neural stimulation intensity levels.

22. The system of claim 14, wherein the means for selecting the at least one electrode and the means for delivering the post myocardial infarction therapy are configured to identify a candidate electrode configuration that provides a discernible effect, and automatically test neural stimulation intensity for the electrode configuration.

* * * * *